(12) United States Patent
Niven

(10) Patent No.: US 7,901,078 B2
(45) Date of Patent: Mar. 8, 2011

(54) OCULAR SCANNING DEVICE WITH PROGRAMMABLE PATTERNS FOR SCANNING

(76) Inventor: Gregg D. Niven, Kaysville, UT (US)

( * ) Notice: Subject to any disclaimer, the term of this patent is extended or adjusted under 35 U.S.C. 154(b) by 499 days.

(21) Appl. No.: 11/880,476

(22) Filed: Jul. 19, 2007

(65) Prior Publication Data

US 2009/0046248 A1 Feb. 19, 2009

Related U.S. Application Data

(60) Provisional application No. 60/832,109, filed on Jul. 19, 2006.

(51) Int. Cl.
*A61B 3/14* (2006.01)
(52) U.S. Cl. .......................... 351/206; 351/205
(58) Field of Classification Search .................. 351/200, 351/205, 206
See application file for complete search history.

(56) References Cited

U.S. PATENT DOCUMENTS

| | | | |
|---|---|---|---|
| 5,512,966 A | 4/1996 | Snook | |
| 5,670,976 A * | 9/1997 | Chiu et al. ...................... | 345/84 |
| 5,864,383 A | 1/1999 | Turner et al. | |
| 5,886,767 A | 3/1999 | Snook | |
| 6,120,150 A | 9/2000 | Sarver et al. | |
| 6,561,648 B2 * | 5/2003 | Thomas ........................ | 351/221 |
| 2002/0180931 A1 * | 12/2002 | Dick et al. .................... | 351/211 |
| 2003/0174928 A1 * | 9/2003 | Huang et al. ................... | 385/18 |
| 2005/0195360 A1 * | 9/2005 | Akita et al. .................... | 351/212 |
| 2006/0203195 A1 * | 9/2006 | Squire et al. ................... | 351/211 |

OTHER PUBLICATIONS

ACMASTER, Optical biometry for the anterior segment of the eye, date unknown.
Bethke, Walt, Catching Pathology: Topography 101, Review of Ophthalmology, Apr. 15, 2004, vol. 11, No. 4, Jobson Publishing L.L.C.
Cains, G. et al., Accuracy of Orbscan II slit-scanning elevation topography, Journal of Cataract and Refractive Surgery, 2002, vol. 28, pp. 2181-2187 (abstract only).
Cairns, G. et al., Assessing the accuracy of Orbscann II post-LASIK: apparent keratectasia is paradoxically associated with anterior chamber depth reduction in successful procedures, Clin Exp Ophthalmology, Apr. 2005, vol. 33, pp. 147-152 (abstract only).
Carvalho, Luis Alberto, A Simple mathematical model for simulation of the human optical system based on in vivo corneal data, Revista Barsileira de Engenharia Biomedica, Apr. 2003, vol. 19, No. 1, pp. 29-37.
Cho, Pauline et al., Repeatability of corneal thickness measurements made by a scanning slit topography system, Ophthalmic and Physiological Optics, Nov. 2002, vol. 22, No. 6, p. 205 (abstract only).

(Continued)

*Primary Examiner* — Joseph Martinez
*Assistant Examiner* — James R Greece
(74) *Attorney, Agent, or Firm* — Clayton, Howarth & Cannon, P.C.

(57) ABSTRACT

A device that projects light rays and beams onto the eye in a predetermined pattern or arrangement of patterns, wherein the light rays or beams scatter in the eye tissues and which images of scatter are captured by video scanning cameras. The images are transferred into digital information for processing, storage, display or retrieval by a processing device which also determines the location, and position of the scattered light in space and prepares a mathematical representation of the light representing the shape, thickness, and relationship of the tissues of the eye.

46 Claims, 4 Drawing Sheets

OTHER PUBLICATIONS

Designs for Vision, Corneal Topography Oculus Keratograph Refractive Surgery or Contact Lens Fitting, date unknown—at least as early as Jul. 2007.

Feldt, Steffi et al., Comparison of ACMaster and OrbscanTM II in Terms of Corneal Thickness and Anterior Chamber Depth Measurements, Carl Zeiss Meditec AG, 2004.

Foulkes, Richard B., MD, LASIK flap thickness is trickier than you think: Regular ultrasound measurements may be deceiving you about the depth of your microkeratome cuts—Part 1 of a two-part article, Ocular Surgery News, May 1, 2002.

Guttman, Cheryl, Rotating Sheimpflug camera provides accurate corneal thickness measurements, EuroTimes, Mar. 2005.

Guttman, Cheryl, New imaging technology provides sharper picture of anterior segment, EuroTimes, Mar. 2005.

Iskander, Nader G., MD, et al., Accuracy of Orbscan pachymetry measurements and DHG ultrasound pachymetry in primary laser in situ keratomileusis and LASIK enhancement procedures, J Cataract Refract Surg, 2001, vol. 27, pp. 681-685 (abstract only).

Liu, Zuguo et al., Evaluation of corneal thickness and topography in normal eyes using the Orbscan corneal topography system, British Journal of Ophthalmology, Jul. 1999, vol. 83, pp. 774-778.

Petrou-Binder, Stefanie, MD, Orbscan II and OLCR laser pachymeter both useful tools for measuring corneal thickness, EuroTimes, Apr. 2004.

Sander, Kristina et al., A study of the effect of the tear film on keratometric measurements with the IOL Master, www.augenklinik.uni-wuerzburg.de/eulib/texte/trfilm/trfilme.htm, at least as early as May 10, 2005.

Sharma, N. et al., Posterior corneal topographic changes after partial flap during laser in situ keratomileusis, British Journal of Ophthalmology, 2003, vol. 87, pp. 160-162.

Sultan, G. et al., Cornea in Marfan Disease: Orbscan and In Vivo Confocal Microscopy Analysis, Investigative Ophthalmology & Visual Science, Jun. 2002, vol. 43, No. 6, pp. 1757-1764.

Wang, L. et al., White-to-white cornea diameter measurements using the eyemetrics program of the ORBSCAN topography system, 2000, 98th Annual Meeting DOG.

Zeiss ACMASTER, Zeiss ACMaster—a new PCI biometry instrument for the anterior eye segment, www.augenklinik.uni-querzburg.de/eulib/acmaster/, Jun. 22, 2004.

* cited by examiner

Pre Focus — Focus

Scheimpflug Focus of Projection System

OCULAR SCANNING DEVICE WITH PROGRAMMABLE PATTERNS FOR SCANNING

CROSS-REFERENCE TO RELATED APPLICATIONS

This application claims the benefit of U.S. Provisional Application No. 60/832,109, filed Jul. 19, 2006, which is hereby incorporated by reference herein in its entirety, including but not limited to those portions that specifically appear hereinafter, the incorporation by reference being made with the following exception: In the event that any portion of the above-referenced application is inconsistent with this application, this application supercedes said above-referenced application.

STATEMENT REGARDING FEDERALLY SPONSORED RESEARCH OR DEVELOPMENT

Not Applicable.

BACKGROUND OF THE INVENTION

1. The Field of the Invention

The present invention relates generally to ophthalmic devices, and more particularly, but not necessarily entirely, to digital ophthalmic devices.

2. Description of Related Art

Slit images were first used for examination of the human eye with the invention of the slit-lamp bio-microscope. These scopes were basically a microscope that allowed the eye tissue to be examined. With these devices, the tissue of interest was placed at the focal plane of the microscope. The first of these devices was invented by an ophthalmologist Alavar Gullstrand in 1911. It was found that if a narrow parallel sided mask was placed in front of the illumination source for the microscope, a slit could be formed and projected into the eye. The physicians found that the slit of light scattered into the tissue as it passed through the transparent tissues of the eye, just as the Tyndall effect is demonstrated with liquids or particles in space. This scattering is a change in spatial distribution of a beam of radiation when it interacts with a surface or a heterogeneous medium, in which interaction there is no change in wavelength or the radiation. This scattering or Tyndall images appear as a uniformly illuminated area that appears to be within the cornea of the eye. This scattering when positioned at various places on the eye would allow the physician to see a curved line of scattered light when looking into the eye. If the position and angle of the slit beam entering the eye was known, it was possible using trigonometry to calculate the relative thickness and distances of the tissues that were illuminated.

The next iteration of the bio-microscope had the mask arrangement built into the illumination system and also fixed the position of the masks such that their exact location was known with a common axis of rotation. Now when the eye was positioned into the focal plane of the bio-microscope, the slit images would also be positioned and the distances and angles easily be measured and known. It was then easier to calculate the distance relationships and thickness of the eye tissues. Because of this slit and lamp arrangement, and ability to closely measure eye tissue, the lamps became known as a slit lamp or slit lamp bio-microscope. Since its creation, the slit lamp bio-microscope has been used for very exhaustive exams of the eye, and over time several filters and attachments have been designed for use with this device, allowing the physician a tool that allows for a comprehensive exam of the eye. Along with more lenses and attachments the physicians have developed several ways to examine specific locations and areas of the eye depending upon the position of the lamp relative to the illumination source and also depending upon the type of illumination, either peripheral, backlighting or surface lighting. Each of these light arrangements yields a different set of images and lighting effects, which help isolate or remove the tissue reflectance, improving tissue scatter or transparency, used in determining an adverse or normal condition in the eye.

Light scatter within the ocular tissue has become a very integral part of this type of exam. The internal scatter of the tissue allows for a fairly uniformly illuminated cross section of the eye tissues. This phenomenon or the Tyndall effect was used in early devices called densitometers and employed in other scientific endeavors. This effect had found use in measuring the opacity or turbulence of liquids such as rivers or streams, angles or distances. The Tyndall effect is shown by understanding that light entering the stream or body of water would pass unimpeded if the water was pure and clean. If dirt, microscopic animal life or other substances were dispersed within the water sample, the light scatter caused by these objects could be seen by a image capture device, such as a camera. A comparison of a clouded image with scatter, against a clear image without scatter could be used to indicate a relationship of how much of a substance is dispersed in the water, where large concentrations are and what concentration is there. A simple sampling of the turbulent water with a count or analysis of the concentration of the material could be attached to the visual readings, creating a table or look up chart based upon scatter vs. concentration of material. Such work has been done in areas such as oceanography, pollution control, soil conservation and the like. This Tyndall effect has become an accepted method of estimating concentrations and distributions of materials within liquids or in air.

By simply applying the Tyndall effect to the study of the eye physicians have been able to create a device that can locate opacities within the human eye vitreous and in transparent tissues of the eye tissues such as with the crystalline lens and the cornea.

At about this same time as the slit lamp was being developed another major breakthrough in the examination of eye tissue was discovered by Theodore Scheimpflug in 1888. An Austrian, he developed, through the study of optics, what is now called the Scheimpflug rule. This rule describes an optical principle of constant focus through a lens, wherein the image and object plane are normal to each other, forming a 90 degree angle. The lens is placed midway between the two planes with the lens at the 45 degree angle. When this arrangement is established, the image and object remained focused on the image plane regardless of object position within its plane. With this new found arrangement, he went on to patent the effect, in 1904 for the use of ophthalmic examination and study. The use of this principle in the examination of the eye has yielded examination photographs of extreme image clarity and focus for tissues extending into the eye such as the crystalline lens.

Presently, some of the devices incorporating this technology are used for the examination of the lens and its opacities. The following work will help explain the theory and show images from this type of device Harold M. Merklinger: Scheimpflug's patent. Photo Techniques, November/December 1996. The first devices used for this type of examination are called scheimpflug cameras.

Scheimpflug cameras have been commercially in use for ophthalmology for the past 25 to 30 years. These devices are unique in that the eye is placed at the center optical axis of the device and at the center of rotation of a rotating head. A camera is placed to one side of the eye on a rotating head at a predetermined angle and is aimed and focused into the eye at a known angle. The rotating head projects a slit of light into the dilated eye of the patient. The camera is positioned such that the exam plane of focus (object plane) is at a right angle to the image plane focus. This preserves the focus of the system and ensures that all images are sharp and clear. During the exam, the slit light source is very intense and is powered by a xenon flash lamp to ensure an adequate amount of light. With each position of the rotating camera head and light source, an image is captured by a video camera. A set of images will be captured from 0 degrees rotation around the optical axis to 180. This amount of images will ensure that the optical portions of the eye are covered for examination. The images can be saved for viewing. The images are then shown and the position of the slit at various angles allows the physician to see into the eye of the patient at various angles, as if a cross section or slice of the eye were made at each angle. This device has been used extensively for the examination of the human eye, especially with regard to an exam of the crystalline lens in an effort to detect cataracts or opacities that form due to age or injury. This exam method allows the physician to take virtual slices of the patient eye for examination. The distances between objects in the eye, and size and thickness of the tissues in the eye are all able to be measured if the eye images are scaled to known and measurable units. Also the intense beams or slits used for the photography, illuminate imperfections in the eye causing scatter where opacities are present, and where air/liquid and tissue interfaces are located. This allows the physician to see, understand and locate any anomalies or imperfections of these tissues and their relationships in the eye.

With this interest in the internal tissues of the eye, other areas of interest in the optical mechanism of the eye such as optical aberrations such as focus or astigmatism requiring correction were also not to be ignored. In 1880, an inventor and physician Placido, found that if a target format of concentric light and dark rings, or mires, were reflected from the surface of the eye and observed, optical irregularities in the corneal surface could be observed. The invention, later called the Placido after its inventor, uses a reflection principle to observe these irregularities. The target or Placido is presented to the eye and the observer looks through a hole in the center ring or bulls-eye of the target. The viewer adjusts the distance to the eye until all mire rings are viewed in focus. Any irregularities in the corneal surface will be manifested by irregularities in the shape, spacing and concentricity of the reflected mires reflected from the patient eye. The appearance is as if a topographic map is made of the eye. If the cornea is spherical and smooth the mire rings will appear to be circular, evenly concentric and regularly spaced. If there are irregularities of the cornea, these will be observed by non-circular, irregular spaced and non concentric ring patterns. The further the mire rings appear from one another, a flattening of the cornea will be present, and if the there is steepening or more curvature change of the cornea, the mire rings will have closer spacing. Because the observed surface of the cornea, the anterior surface, is the surface that most controls the focus of the eye, any irregularities that are observed by direct observation or in images, can be used by the physician to determine and explain the optical aberrations observed by the patient. Devices based upon this technology have found widespread use for examination and diagnosis of eye anomalies. Its function for better and in depth eye measurement is limited however in that it is only a topographic device that examines the external surface of the cornea and that does not account for the corneal posterior surface contribution to the optical irregularities that are observed. Also there are several corneal anomalies which have been determined to occur in the posterior cornea which lead to aberration and vision failure that can not be readily observed with an anterior corneal measuring device. Because the cornea's posterior surface contribution to the overall vision prescription is about ½ of a diopter in correction, the physician will never fully arrive at a full understanding of the patient's corneal aberrations and how they affect the entire vision prescription for the patient. Additionally, the physician will be unable to observe corneal failures or other defects in early stages of development without a direct observation of the posterior surfaces of the cornea. Another drawback to these Placido-based mire ring devices is that due to the shape of the cornea, the measured shape of the eye can be tricked or mis-diagnosed by the physics of the design. Because we are observing reflected light, rays of light can appear to emanate from more than location on the mire ring or Placido. This problem that has been named the twist angle by developers in the field, is known and understood. Several manufacturers of these devices have undertaken creative solutions to help alleviate the problem, by using variously colored mire rings, square shapes, radiating line patterns etc. to overcome this error. Progress has been made in removing this latter problem, but there still remains the first problem, in that these devices as designed still can map only the anterior or front of the cornea. Another factor with using this type of device, is that the distance from the eye during image capture, has a significant effect upon the calculated distances. Such devices are calibrated by use of a reflective sphere of a known radius and image data that is captured is compared to the known data to determine the differences. With the differences known, the eye result is calculated based upon this difference. These devices are subject to error in that if the distance to the eye is slightly different than the calibration sphere was, the radius calculation for the difference in distance has an effect on the calculated sphere diameter, due to the differences of calibration and captured image. Thus with these Placido-based systems, it is critical that exact distances be repeated from subject eye to calibration sphere. Devices that employ this technology, have also undertaken methods to overcome this shortcoming such as triangulated dots on the cornea, extra rings etc.

As for measurement of the corneal thickness in order to understand and diagnose corneal anomalies, there has also been progress made. The first non-contact methods of corneal thickness measurement were performed with a slit lamp biomicroscope. In this process, a narrow slit of light is projected into the eye at a known angle forming a Tyndall image. A gracticule that is graduated in microns is placed in the eyepiece of the slit lamp. The width of the Tyndall image is measured with the graticule and by simple trigonometric calculations, a thickness can be determined. This type of examination is tedious and to get any true understanding of the overall corneal shape would require hours of examination and calculation time. Other non-contact methods are the Scheimpflug camera, which would also require a large amount of time for examination and calculation. Also, these devices, are designed to emit amounts of light into the eye, which allow for good visualization by the physician, but with long duration can be detrimental to the long-term health of the patient eye. Other than these methods to this time, the only other way to measure thickness was to use ultrasound measurements wherein changes of time delay from reflection of high frequency sound is waves are used to identify boundary layers such as the anterior surface of the cornea. The drawback to this methodology is that it is a contact method, and that as yet, there is not a way to measure truly and to calibrate devices to accurately measure in-vivo eye tissues. For non-contact thickness measurements, the field is quite narrow for choices open to the physician. However, within the last 12 years two significant devices for more thorough automated corneal examination have been developed and are on the market. These devices use a combination of technologies heretofore explained but gather and use this information in different ways.

One system, called the Orbscan,™ (Bausch & Lomb) is one such device. Originally designed as an optical densitometer, (Snook U.S. Pat. No. 5,512,966, Sarver et al, U.S. Pat. No. 6,120,150, Turner et al U.S. Pat. No. 5,864,383), it was found that this device could be used to map the locations of opacity and scatter within the eye. After experimentation it was found that the device could be used to locate boundaries of the scattered light and create maps of thickness if the distance between boundary layers could be calculated. This device uses a projection system, which includes a bulb, lens and a moving mask system. This mask is a parallel lined mask oriented vertically when projected onto the human eye. This mask, the object, is moved in a linear direction that is oriented in a plane that is normal to the image plane. The image plane for projection is located just inside the cornea of a human eye and is oriented parallel to the iris plane of the eye. This orientation between the object plane and image plane is established as a Scheimpflug relationship and follows the Scheimpflug rule. Due to this relationship, a linear motion of the mask yields an equal transverse motion of the slit light upon the eye, and while doing so remains in focus, on the pre-determined plane. Due to the Scheimpflug relationship, the image plane is always in focus. If an image capture device such as is used in the Orbscan, was to be focused to and was used to observe the image plane in the eye, all images that were captured could be focused easily and remain in focus during an exam.

When used for examination, the Orbscan device is placed at a predetermined focal distance away from the patient's eye determined by the optical properties of its lens system. Two controllable slit masks as previously described are placed on a plane each side of the optical system in the Orbscan, and are projected into the eye on an image plane as described, angling into the eye tissue at of 45 degrees off the center axis from each side. The video recording device, a camera is placed in between the mask projection systems on a central optical axis. The system is aligned by placing the optical axis of the system in alignment with the optical axis of the eye being examined while simultaneously being focusing the system at the image plane of the projected slit images. The images produced are Tyndall images which are illuminated cross sections of the subject eye, where in the scatter within the tissue is easily seen. The patient fixates his/her eye into the optical device system which brings the optical systems of eye and device in alignment. After being positioned thus, the exam commences. The illumination lamp output is focused by the condenser lens and focused through the mask, off of a mirror and into the eye tissue. the lamp illumination is commenced while each of the masks are positioned at pre-determined locations for starting. Following initial position, each mask is moved to another successive position fixed and moved again until each has completed its cycle of range positioning. Each position of the mask is controlled by a computer and hardware interface which synchronizes the image capture function of the system to the illuminated positions on the eye. There are 20 positioned Tyndall images taken for each lamp/mask combination, totaling 40 positions and 40 sets of Tyndall image data.

The image data is then processed using proprietary algorithms to locate boundary edges based in the Tyndall images. Once boundaries are found, sizes, distances and physical relationships of eye tissue can be determined. The data is graphically rendered to form a mathematical representation of the eye and internal eye tissues. The information is then available to be displayed, printed and stored.

The drawbacks to this device involve these issues: 1) A dis-association of side data, from the true center data; 2) The amount of time required to take an exam, and mechanically position the mask for each successive position within the exam contributes to patient movement and eye motion increasing the error of the result; 3) The mechanical tolerances of mask position error cause variation and error in the final result calculation; 4) The change in angle of incidence as the light strikes the curved surfaces of the cornea is not calculated, and contributes to total system error; 5) The amount of time, effort and variation caused by human error during device assembly, alignment and calibration, also cause variations from one device to another; 6) Variations in the final resulting data due to changes of the opto-mechanical parts over time and use such as apertures, illumination intensity variations, positional location variation, and voltage variations and losses.

These six issues will be dealt with in order. The first disadvantage is the fact that the Orbscan device has two masks and projector systems each operating independently from one another. These masks and associated image capture systems each see the eye from a different respective location. The two systems are basically two different systems being linked together with a common base plate and capture system. This perspective of view creates two different viewpoints and makes it harder to help the curves appear to be on the same plane. Since they are also calculated separately and later joined, there are errors introduced into the surface calculations due to this average or combining that occurs. These surfaces essentially are two surfaces that are forced into alignment. The boundary areas between these surfaces can become distorted or even lost when these surfaces are joined. To help overcome some of this error, the Orbscan uses a Placido or ring reflection device for calculation of the outer boundary radius to which these two curved surfaces could be molded to.

This fix has a tendency to be prone to error as a Placido ring reflection device is very susceptible to distance location calculations from the eye. A small error in exact location of the Placido from the eye, changes the radius of eye curvature, thereby affecting the position and radius of the two disjointed surfaces. Another issue that is a drawback to the Orbscan device is the time taken to position a slit mask, settle it in position for an image capture, capture the image and move it again takes several seconds over the course of the entire exam. It is virtually impossible to keep the human eye still during this time. Regardless of the ability of a patient to remain still, the human eye moves in small random amounts called microsaccade motion. The eye performs this correction or motion an average of 60 motions per second. This motion allows the eye nerves to be stimulated while staring at objects and which allows the macula, or more sensitive part of the retina to observe the images better. During the time of the exam, the patient is fixated upon a target which requires staring or fixing of the eye. During this time the eye is moving with microsaccadic random motion without knowledge of the patient and without a detection method of the Orbscan. Because of this motion, it is virtually impossible for the eye to remain stable during the exam. This motion is a variable from one patient to another, adding to the variance from patient to patient and from one eye to another. Another factor that contributes to error is that the eye actually changes diameter during the exam due to the heart rate and ocular pressure of the patient. These variances force the calculations to be more averages rather than exact measurements of the eye and eye tissues. The physicians using these devices require accurate information with which to prepare a surgical treatment or diagnose a malady or even determine if the eye is normal. Minute changes, errors or variances in this information can cause optical parameters to change thereby affecting the outcome. The Orbscan device has been shown to have variances from machine to machine. The physicians are demanding that the variance be removed as far as possible from the measurement results.

The next issue is the fact that the Orbscan device uses mechanical stepper motors and slides to create a linear motion and position system for the masks. These individual components are subject to commercial manufacturing tolerances and these tolerances vary from one component to another. When all these components are brought together, they create a background amount of variability that is important to overcome. The Orbscan device uses a calibration process to unify the components for each individual machine. This data variation is supported as there is consistency within a machine, but variance from machine to machine. The population of machines produced can be affected by a change in tolerances and such tolerances will tend to show up as variation in the final result. Consequently, we see these variations in measurement and in statistical results. Other issues that can affect performance of this device is the relative change in incidence angle and its affect on the calculations for thickness and location of ocular tissues in the eye. The human eye is not a flat surface and as such the light entering the eye from a fixed location and angle is subject to the variations of the corneal shape. These variations will be evidenced by variations in the corneal thickness across the eye even if these variations in the actual tissue don't exist. This aspect of the Orbscan measurements are not taken into consideration, as the present system does not have the capability to do so. The two remaining drawbacks are that mechanical performance of devices change over time. These variances may be due to shipment vibration, wear, age of lubricants, dust, filament aging due to use, etc. Each of these issues are a variable which affects the long term performance of the device and its accuracy. Additionally, much of the adjustment required for the device is external manual adjustments. This variability from assembler to assembler will affect the baseline performance for the device, both individually and statistically across the population.

The Pentacam™ (Oculus) device is basically a diode illuminated Scheimpflug camera. This device is a small device based upon the previous technology used in Scheimpflug photography. The theory behind this device is the same as the other previous Scheimpflug devices. The difference is the application of a diode illumination system instead of the flash lamp. The diode illumination system has a real advantage over traditional incandescent light sources. The wavelength in this device is ranged more toward the shorter wavelength or blue end of the visual spectrum, which has a tendency to create more scatter within the tissues of the eye. The other advantage to this system is that the images produced are deep, meaning they range from the cornea to the back of the lens, and they are highly focused. This device exam is done the same way as the older Scheimpflug camera, in that the patient is positioned in front of the optical head with the eye on the optical axis. The exam commences and the camera is rotated around the eye at 5-10 degree intervals for 180 degrees. The data is captured and the surfaces are calculated. This device has found great acceptance however there are drawbacks as we shall discuss. The exam is shorter in duration than the Orbscan device but is also long enough that the eye motion is a factor.

The drawbacks to this technology are 1) there is a problem of determining the true center axis to rotate around. If the eye moves at all, it is lost. 2) the time for the exam takes too long allowing eye motion to be a factor in the results. As the eye is focused at the center, this device requires an axis center to rotate around. The high point of the cornea, or apex of the eye is not always the accurate place as it is sometimes off the center and not on the optical axis. In most human subjects the iris plane is not normal to the optical axis of the eye. This is referred to as angle kappa. This aspect of the eye orientation to bring the macula into position for good vision, causes a point that is not the apex of the cornea with respect to the iris plane to be the high point. Because of this, an artificial rotational axis has to be located and used. This hopefully is aligned with the optical axis of the eye. This axis can be created by reflex reflections on various surfaces to align by, but if the eye moves a small amount, this point is moved and consequently all maps that require the center to be matched to cannot be accurately mapped and placed upon the center. This causes the software to determine an average point to set all exams to. With this average location, a compromise in the surfaces will be obtained, and results will not be accurate. This has actually been witnessed in the use of this device. The photographs and images are pristine; the data has less than expected accuracy.

Several devices have been developed to increase the accuracy of the above devices such as using a mask controlled by an LCD array. This is a novel approach but is flawed in that the devices proposed, provide diffraction at each aperture. The apertures being small have a tendency to diffract the light making the image more irregular and non uniform. The other drawbacks are that the device polarizes light as it exits. Polarized light may provide one direction of light scatter, but may prove to have high loss in other directions or on other surfaces. This has yet to be proved. Another issue is the amount of efficiency of the light traveling through the apertures yields a loss on the order of 60 percent. This makes the machine more un-gamely and large due to increased lamp size and efficiency.

This discussion of these devices shows that the data obtained from present devices needs accuracy to place the surfaces in an orientation and location that is accurately positioned with regard to the optical axis of the eye. This error in data and mapping is not possible due to the time required for exams, and due to the fact that the data maps do not have a method of tying the data together that is accurate. Also we see that the data gathered is related to the manufacturing tolerances and positional error due to mechanical controls.

What is needed is a device that eliminates as much as possible any mechanical device for positioning and also allows quick fractional second acquisition of the data. There also has to be a method of tying the data surfaces together in order to provide a mesh of data that does not rely on the positional location obtained by tracking of the eye. Also there needs to be a feature that allows the device to accommodate differing colors of irises and allow an overall exam of the eye for sizing and metrics. Other features not present in the previously available designs such as internet upgrades, different custom patterns would also be desirable.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
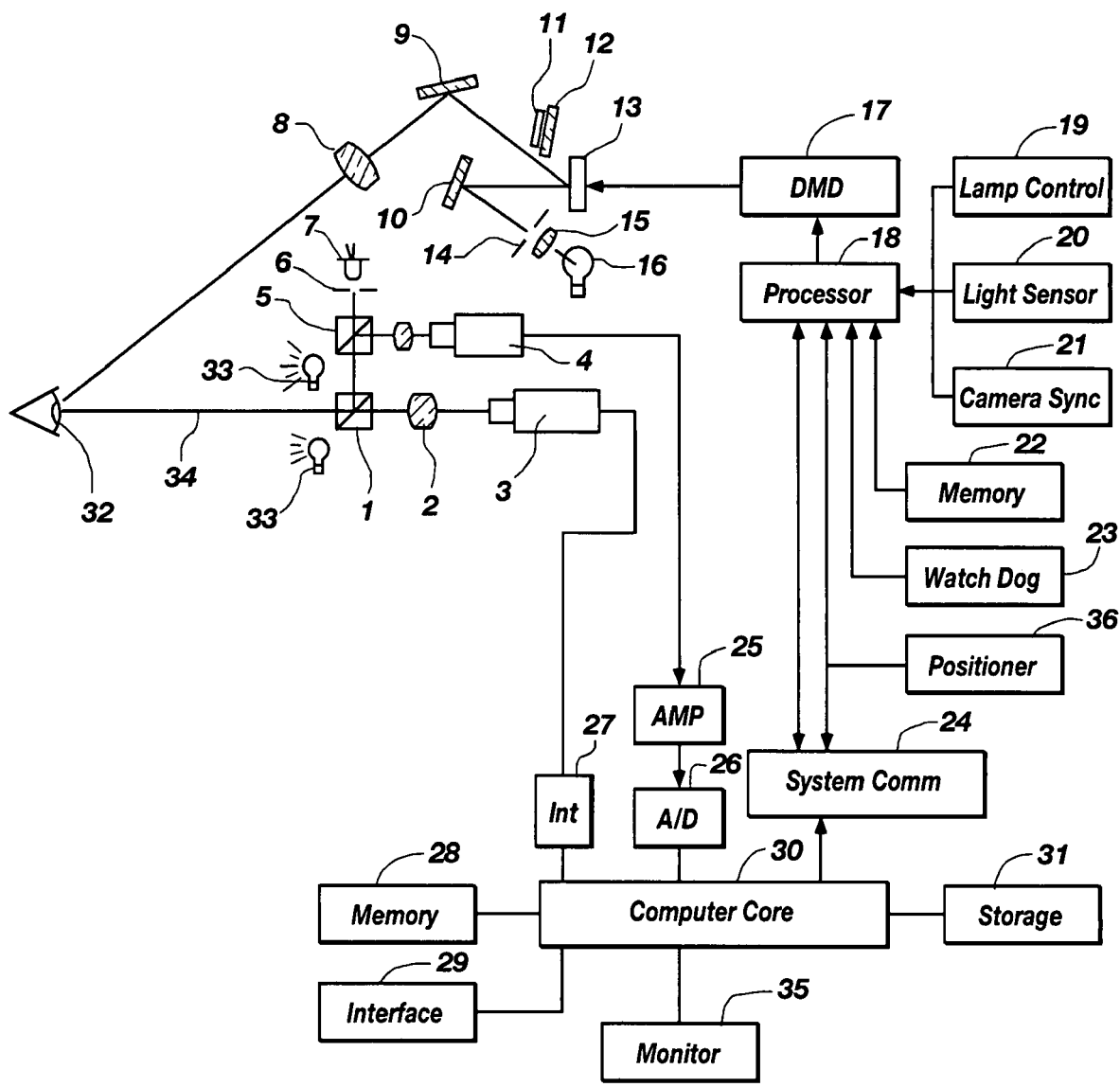
FIG. 1 is illustrates a diagram of an exemplary embodiment of the present invention.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise. As used herein, the terms "comprising," "including," "containing," "characterized by," "having," and grammatical equivalents thereof are inclusive or open-ended terms that do not exclude additional, unrecited elements or method steps.

The device embodied within this application comprises of devices and controllers that overcome the limitations presented in the previous work. The proposed device consists of the following sub sections, each with its own function.

The heart of this device is the mirror control. The mirrors consist of an optical semiconductor chip. One form of these chips comprises tiny mechanical mirrors of about 3-10 microns in an array of at least 1024 L×768 H mirrors total. Each mirror is small enough that it can be smaller than a pixel when being viewed on video or in projection. Each mirror is independently addressable, by software control and can operate independently of surrounding mirrors. Each mirror has an ON position which represents an angle of the mirror that will allow light to be reflected from the mirror surface into the projection and focus system of the device for final projection into the eye. The OFF position represents a position that directs light reflection away from the projection system, typically into a light dump or sensor. Standby position is a mirror position that allows the mirror face to be parallel to the chip base mount.

The action of this system allows each mirror or an array of mirrors to be controlled in formation, or combination with one another based upon the software control supplied to the mirror array. The mirror array chip is part of a set of chips that control the function of the mirrors. The chip set allows each mirror to be addressed and controlled with a microprocessor, or by video control if that is what is desired. The set of chips provide the needed interface. Each of the mirrors are coated to reflect broad visible spectrums of light. With the peak reflection coating of sodium D. The mirrors could be designed to reflect other wavelengths such as longer toward the red end of the spectrum or more towards blue and ultraviolet. Because differing tissues of the eye have different refraction and reflection characteristics various wavelengths may be desirable for assessment of different ocular areas and pathologies.

The presently available devices have only a controlled single motion, set width slit of light. Through experimentation, it has been determined that other patterns of light might be desirable as well as differing widths if slits can be used and are more effective in intra-cellular layer detection in the eye tissues, as well as for the prevention of backscatter and intensity that might interfere with the light reflection measurements. The other advantage to using the mirror array is that slits or coordinated patterns of light may be projected and travel in any manner or way onto the eye. Unlike the other designs, this pattern is not limited by mechanical control, but software control. The various slits or controlled patterns can be coordinated to project in a pattern that is based upon the position on the cornea, the tear film breakup and any other pathology desired to be reviewed.

The drawback to the other devices is removed with this device. The motion controlling portions of the device are removed as are toleranced parts that move them and position them. This will result in a marked benefit that will be realized with less variance in actual use. The other advantage of this device is the reduced time required for positioning of patterns or slits, resulting in faster exams and less chance of saccadic motion of the eye.

A projector assembly consists of a light source, either LED lamp or halogen that is placed behind a condensing lens at its focal point as with a Köhler projection system. When the lamp or light source is illuminated, the lens takes the light and captures all light from the accepted angle of the lens and creates parallel beam or rays of light in an expanded diameter and evenly dispersed pattern. This pattern is projected onto the mirror array evenly illuminating it overall. When the mirrors are activated to the ON position, the light will be reflected into the focusing optics. Since the entire mirror array is illuminated, the mirrors can be controlled to be ON in any pattern or combination and the resultant light will appear as lines or patterns that can be moved, translated or strobed to illuminate only what is needed. This process allows the patterns to have a predictable amount of light available to illuminate the target which is the cornea of the eye. Another advantage to the light sources is that they can remain ON during any aspect of the image acquisition process, allowing the lamp to operate in a stable predictable fashion. Alternatively if flashing lights or strobing is required, the mirrors may perform that function independently of the light source.

The other advantage to the mirror control is that a light sensing device such as a detector, silicone cell or the like may be positioned in a location wherein the light reflected when the mirrors are OFF may be detected and measured or calibrated. This eliminates degradation of the device function due to lamp age or light degradation, even line losses in power input. Another benefit to this arrangement is that light levels can be changed on the fly. This adjustment will be beneficial due to the fact that many patients have different colors or iris pigments. Dark irises have minor affects on eye measurements using light whereas light pigmented irises, have more scatter and reflection from the iris causing more potential reading differences and errors due to the light interference from scatter of other surfaces.

Another benefit is the variances in lamp performance can be negated as the intensity can be measured prior to the exam and lamp levels may be adjusted to compensate. Presently in the Orbscan device, the device has an iris to set the lamps or light sources within selected ranges for optimum performance. These irises are subject to diameter change due to vibration. This is another item that can remove variability from the system.

A color wheel or a colored filter may be used to change the color of the light. The term "telecentric" means a cone of rays emanating from an object point that remain perfectly perpendicular to the object plane across the entire field-of-view.

Optical focus system is used to focus the images created by the mirror onto the eye tissues. This focus system ensures that the images presented to the eye and captured from the eye are in sharp focus. The focus of the image capture device is as important as ensuring that images are focused when projected. The software will use the focused images for a determination of the edges of the patterns or slits in determining the true location, shape or position of the corneal tissues. The focus system will have a lens that is capable of presenting and maintaining flat images, that are free from distortion. This will allow the mirror array and mirror images reflected to remain in focus during the exam process. Another requirement of the focus system is to project an image on the eye that has a depth of field deep enough for hitting the iris sharply while also staying in focus as the images traverse on the eye. A multiple element lens will be sufficient to perform this task however a more complex element lens will ensure that the images remain in focus. This system is arranged such that the imager and eye are arranged in a Scheimpflug pattern to ensure that the images and objects are always in focus.

This device will also use one or more image capture devices. One may be a lower speed lower resolution device whereas one might be a high speed image capture camera that can actually capture images at frame rates approaching high speed photography. A desired speed of capture will be approaching 200 to 300 frames per second. A conventional video camera may also be used, but lower frame rates will require more time for capture and processing. The camera will require a large format image capture device or CCD array that has enough resolution to be able to see the images on the eye sharply and distinctly. This array will also require pixel size small enough that images captured will indeed remain in focus without added degradation due to image size changes and due to pixel sizes and registration. The camera chosen will require the compatibility of the light sources. This will allow different images to be captured based upon light wavelengths chosen. A desired camera is one that will be sensitive in the visual and near infrared. Many camera devices are on the market that have this capability.

One device can be placed on center with the optical axis of the device with another one place using a beam splitter or placed off axis. This will ensure that the images obtained will be confocal to the camera and will remain in focus without having to re-position the machine. If multiple cameras are placed off axis at opposing sides of the device, exam time can be shortened even more then present, due to the cameras working simultaneously and capturing the image form two locations, causing a true 3-D dimension capture of image data.

This present device works with the cameras and processor to capture in a synchronized manner images obtained by the camera. This present device has storage capacity and interface capacity to allow images to be streamed into memory at controlled intervals. It also allows the processor to access the data that is captured for use in processing images and surfaces and also for use in display printing and transfer. This data consists of captured video images that are translated into a storage format.

The processing device may consist of a computer or other processing device that also serves functions in control and communications. This device shall control the function of the device, control communications with other devices, use and apply algorithms to the processing of captured data, process data into maps and images used for viewing and imaging. The processor also controls by software interface the ability to allow users to control functions such as printing, storage, database control and maintenance and also the transfer of data to other devices and users.

The storage device consists of an internal hard drive or an external storage place or device. If it is remote or external the device will communicate by internet communications or by intranet communications.

A display device consisting of a computer monitor, or other image forming device, which takes processed data and displays in a manner that the user can interpret, and review the information that is presented.

An input device may comprise a keyboard, a computer mouse, or voice recognition system.

These parts make up one embodiment, and other devices or substitutions of these devices may be used to provide more adequate data processing, capture or manipulation for better diagnosis and treatment use with the machine.

Referring now to FIG. 1, there is shown an exemplary embodiment of the present invention. To operate the system, the computer system core 30, interfaces 27, memory 28 and storage 31 are powered on. This initialization will also power up processor 18 and associated parts. In this device, 8 lens 8, mirror 9, sensor 11, filter 12, micromicron array 13, mirror 10 and light projector assembly 14, 15, and 16 are mirrored on the other side of the optical axis. This arrangement is on a common base plate creating a plane that allows all devices to be placed commonly in front of the patient. The operation of the device allows for use of both sides of the projection system and all work in conjunction with the processor 18 and mirror array driver 17. The computer core 30 is brought on line working a pre-arranged program set, that prepares for alignment, image capture, data calculation and data display.

The patient is positioned to allow an eye 32 to be positioned along the optical axis 34. The positioning may require structure to receive part of the patients head, such as a chin rest or a restraint. During the focus cycle, the lamps 16 and 33 may be illuminated and the processor 18 and mirror driver 17 allow for a pattern of light to be emitted and projected to the system focal plane where the patient eye will be positioned. The device may be manually positioned by an operator to bring the eye 32 into focus by using light patterns that are projected upon the cornea of the eye. Focus of the device is verified by the operator observing images captured with camera 3 or 4 and displayed upon a monitor 35.

Figure 2:
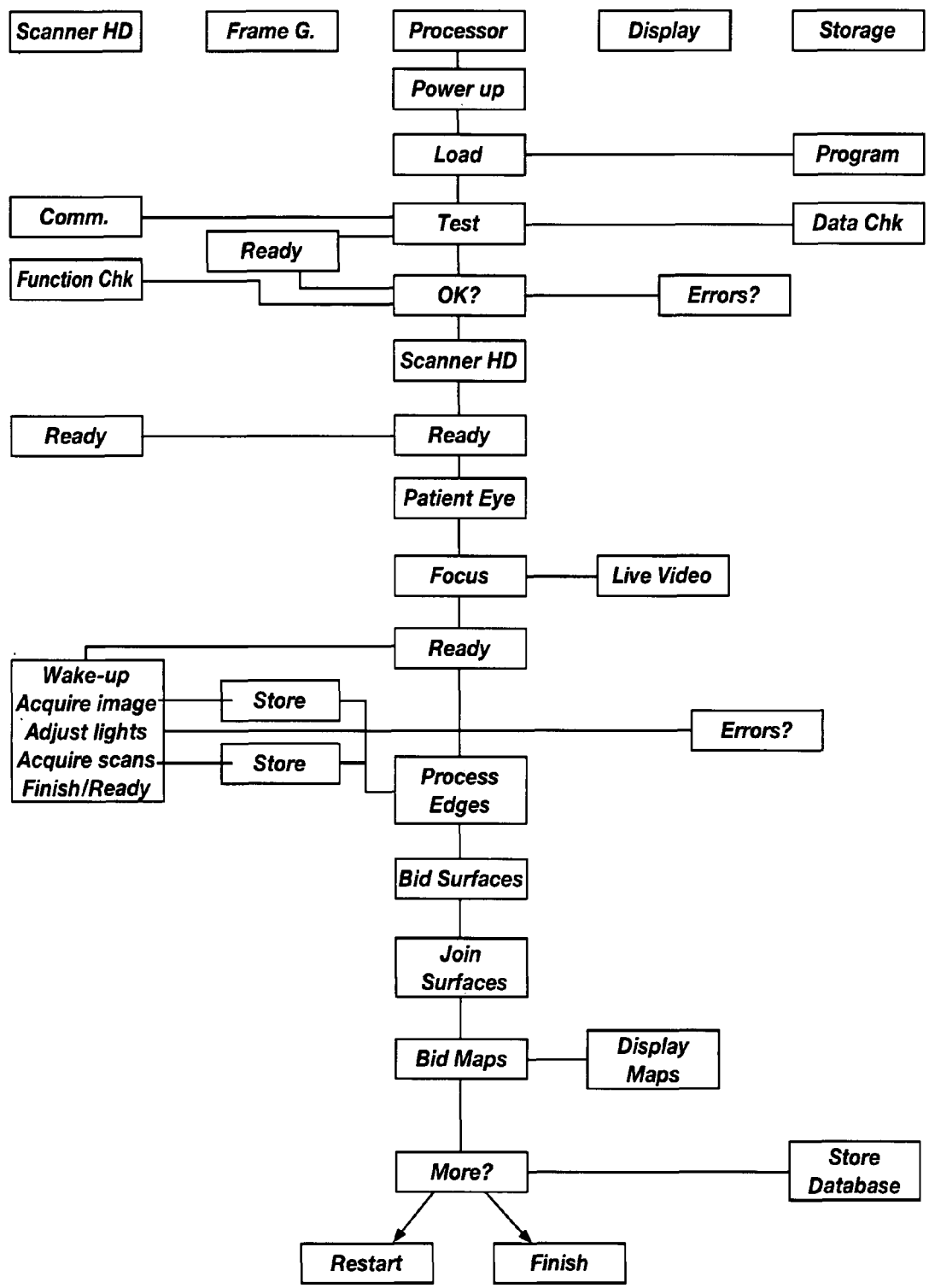
FIG. 2 is a flow chart.
Figure 3:
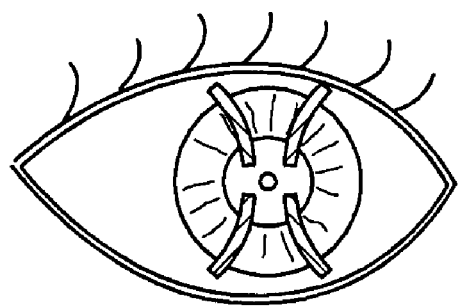
FIG. 3 shows a focusing procedure.
Figure 3:
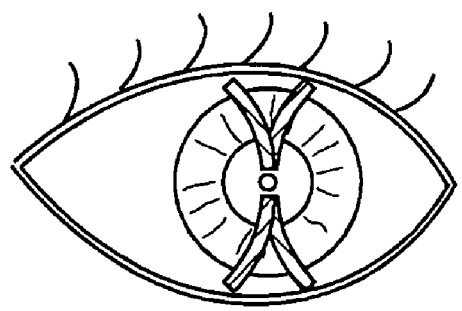
Figure 4:
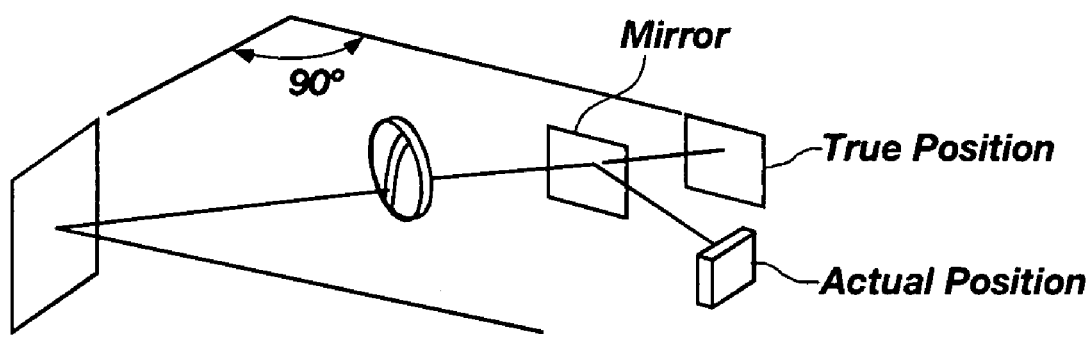
FIG. 4 is a Scheimpflug focus projection system.
Figure 5:
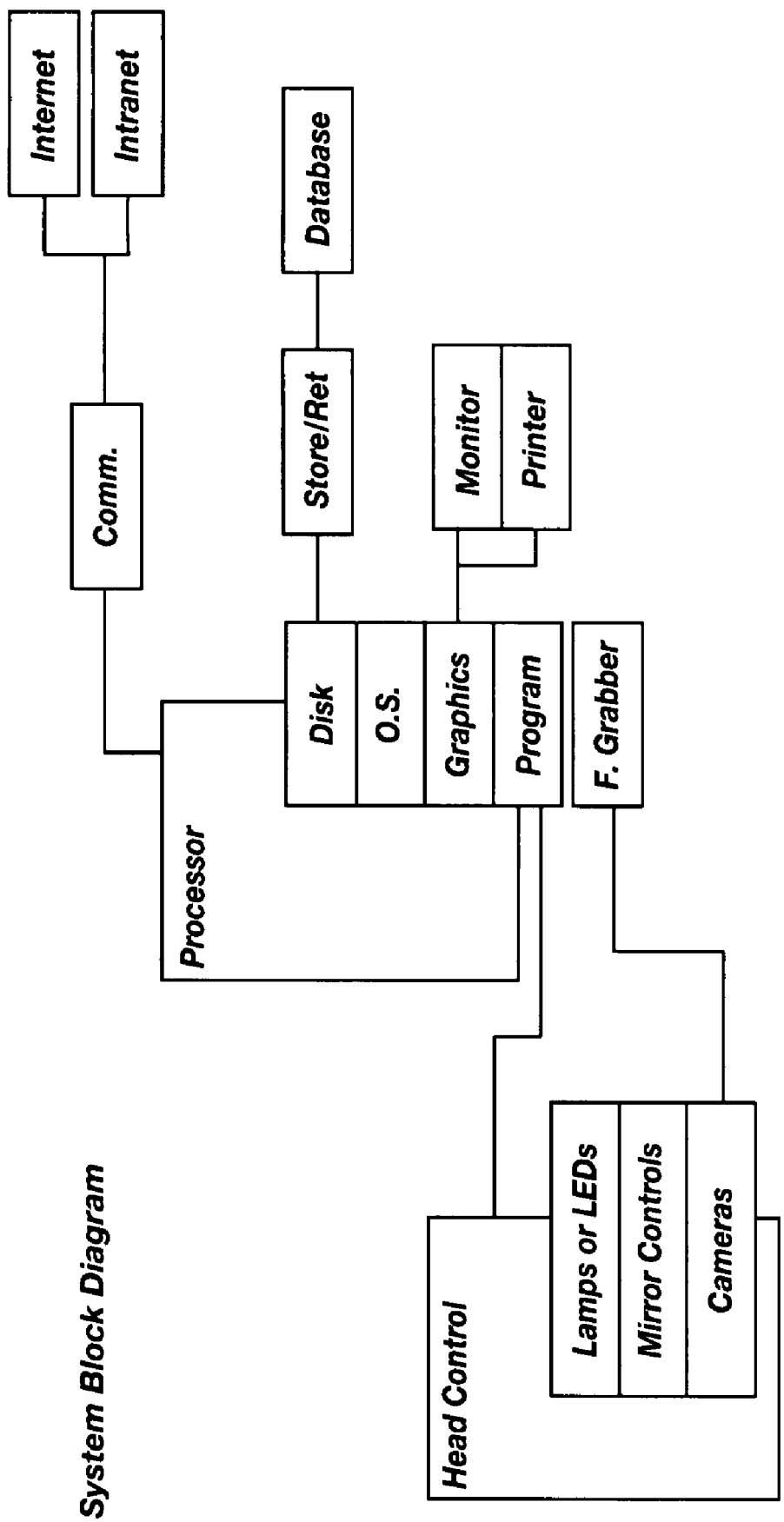
FIG. 5 is a system block diagram.

Camera 3 is used for examination, but also may be used for focus, should only one camera be desired for operation. Camera 3 may be an analog color camera or black and white imaging camera. Camera 4 is combined with the optical path 34 by means of beam splitting cubes 1 and 5. Correct location for focus will be determined by the patterns observed on the monitor as described in FIG. 2.

Other patterns or images may be used to determine correct location or focus. Also, this aspect of the focus may be performed by the device itself using automated positioned 36, should that be included. Further a lens assembly may be provided for focusing.

The patient is asked to observe image 6 illuminated by lamp 7 that appears to be inside the device. Lamps 33 are used to provide base line light levels for comparison, adjustment and to remove various room light level settings. While the focus is being performed, the mirror array 13 allows the remainder of the light not used for pattern projection to be positioned upon the light sensor 11, thru filter 12. The lamp sensor 11 communicates with sensor control 20 and lamp control 19 inside processor 18. Lamp values illumination values are adjusted to compensate for lamp voltage settings, room background illumination, eye color, and changes to illumination caused by aging of the lamp. Once the device is focused and light values are set, the capture sequence may begin.

Capture initialization may be automated if all predetermined criteria is met, or may be manually started by the operator. The initialization for capture begins by routines in the program starting the processor 18 operation and control of the mirror array controller 17. The processor also communicates with camera 3, with camera sync 21 and with core 30 thru interface 24. The capture program will instruct mirror array 13 to allow a light pattern to be projected upon the eye, communicate to camera 3 to capture the image of the light pattern on eye 32, thru the interface 27 and dump into memory 28 the data that camera 3 captured. Following this capture, the mirror array 13 is turned "off" preventing light from lamp 16 to strike the cornea of eye 32. While the data is being dumped to memory, the other side of the device, as described above is presenting an image to the eye, the data captured and the dump started. once the dump is started, array 13, is again turned "on" to allow another pattern to be projected upon the cornea of eye 32. This alternating pattern of projecting, capture, dump, allows the capture to occur at a high rate of speed limited only by the speed of the electronic devices, and the speed by which the data can be placed into the memory for processing. The patterns presented on the eye are controlled by the processor 18, and can be changed to virtually any pattern depending upon the information provided to the mirror array driver in the form of an image code, that is given to processor 18 and downloaded from the computer core 30 from storage 31. The image code may be streamed to the mirror control. Each mirror in the array 13 is individually addressable through the mirror driver 17 and based upon the quantity of mirrors, the speed at which the mirrors controlled, an unlimited amount of patterns can be generated, for presentation to the eye. The images and data collected are limited to the amount of patterns desired, the amount of data desired and what is needed for accurate representation of the eye in data.

After the data is captured and placed into memory 28, the computer core will initialize the computational portion of the program steps. Each of the digital images will be evaluated to determine the location, width and shape of the light patterns on the cornea. Once the locations and width of the patterns are determined, an array of digital points in space can be made to represent the shape and form of the anterior portion of the eye. Since the measurements can be scaled based upon a calibration set of data and upon the geometry of the system, true measurements of the eye can be made.

The data information of the eye is then placed into a graphical format for display upon the monitor 35 which allows the a practitioner to review, examine and make diagnosis decisions about the patient eye. These images can be stored, transferred and used for records and other needs for the patient and practitioner.

The software required to run the embodiment may comprise several modules as described below.

Calibration Module: Section for testing function, setup, alignment and replacement of components.

Entire Image Capture Module: Eye image capture that acquires eye when system is focused and ready for capture. This image is used for measuring diameters edges, boundaries etc.

Iris Calibration and Recognition Module: Section of code for iris recognition and for calibration of light values, will require interaction with mirror controller, light sensor and lamp control.

Positioning and Focusing Module: Code section that will be used for help in positioning the eye images prior to acquiring data and images. Will interact with framegrabber, controller and with visual system for acquisition.

Pre-Acquire Setup Module: Targeting of areas of the streaming images used for triggering an exam. Will set boundaries, edges or other artifacts to be used for the trigger process.

Mirror Control Module: Code used for the synchronizing, position and control of mirrors on the device, required communication with the D.P. mirror controller and mirror chip and stored data for image presentation.

Image Capture Module: The process of synchronizing position, of lines with camera frame capture, to capture images of the eye and the storing of said images into memory in the capture card or in computer memory. Interaction with the processor, framegrabber, camera and controller card.

Image Store Module: Moving the image data from active memory into more permanent memory to allow time for processing, building and other functions regarding storage Image Processing Module: Code used for determining the location of boundary edges of the light in the images. (edge detection) And the assignment of numerical values for those edges, so they can be used for surface construction and mathematical models of the tissue surfaces.

Surface Builds Module: Code used for building 3 dimensional surfaces based upon the numerical values for the boundary edges. These surfaces are mathematical representations of the tissues of the eye.

Surface Join Module: Code that takes the surfaces and joins them together into a seamless surface that is representative of the whole group eye surfaces and tissues.

Data Mapping Module: Compilation of a map that represents the complete surfaces generated in a finished form. This map is a mathematical representation of all the eye surfaces that were detected and created.

Image Build Module: The code used to build an image of the eye in a format that has colors, values or other representations to simulate the surfaces and tissues of the eye.

Map Generation and Data Display Modules: The code used to generate colored maps topographical maps or representations of the eye, this process assigns colors for numbers and generates maps for visual display and printing. Maps could consist of differences between exams, surfaces or other features, also could be cross sections, 3 dimensional representations, graphs charts, measurements etc.

Store, Print, Display, Translate, and Transfer Modules: Data manipulation for storage, transfer, communication display send translate etc.

Database Control Modules: Control of the information gathered into a database that allows sorting, storage, retrieval, number assignment, searching and analysis.

GUI: Code that interacts with the OS in displaying options, controls etc for user interface Device Head Imbedded Code Control Module: Code that is located within the device used for control, error handling, booting communication, mirror and light control and sensing. Also interfaces with cameras to ensure that the timing is correctly synchronized between devices.

How the device will interact with the user, patient and with various components is described below:

1. Position the eye in front of the optical axis of the machine at a predetermined location of focus.
2. Patient fixates upon distant appearing target.
3. Focus the machine either by eye or automatically if so equipped.
4. Power up lamps.
5. Locate center of eye, optical axis using dot or focus system allowing patient to see at distance.
6. Image capture of eye without exam data for iris
7. Determine light amount required (dark or light iris) necessary for best possible exam.
8. Energize the mirror array.
9. Pass pattern of light on/into tissues of the eye in sync with capture device and camera 1 position, 1 image stored.
10. Complete exam of thin slits or patterns on middle, thick on periphery, and horizontal pattern to tie together.
11. Transfer information to processor.
12. Apply algorithm processing to data captured to locate edges of the light scatter beams.
13. Locate edges.
14. Generate mathematical shape for all surfaces captured with each capture device. Vary angle of data based upon curvature position of eye. Determined by horizontal slit.
15. Use horizontal mathematical surface shape to combine sides.
16. Create 3 dimensional math representation of tissue locations in the eye.
17. Apply colors or other representations to map to delineate and show locations, and relationships of eye tissues.
18. Display image on monitor or screen.
19. Store or print information into hardcopy map.

Further, communication of the images may be made over the internet, allowing more research and maps to be delivered without technical help. Outputs into formats used in digital record keeping or into formats to be used with a laser or other treatment or ablation devices.

The device may also allow realtime imaging during surgical procedures if cornea is not disturbed such as with a intracorneal treatment device. Or during cataract or phacic procedure to re-establish corneal shape after and during suturing.

Some of the advantages of the present invention are detailed below:

1. Faster focus procedure either automatic capture, or auto focus.
2. Whole eye capture with iris recognition for record retrieval and processing.
3. Automatic compensation for iris colors.
4. Automatic compensation for bulb aging or dust and dirt buildup.
5. Automatic calibration, all features built in modular replacement capability.
6. No mechanical components to wear or to age or change during use or shipment.
7. Variable patterns of light presented to the eye, circles, lines, bars, squares etc.
8. Variable pattern of light motion, unrestrained due to the mirrors.
9. Variable thickness or changes to lights on the fly, can change width, angle or remove sections if desirable.
10. Joins data surfaces by common exam method, horizontal, angled, circular, etc.
11. Upgrades to system on the fly, no technician required.
12. Removal of tolerance variations due to manufacturing.
13. Removal of variability in finished systems due to operator and assembler error.
14. Use of various wavelengths of light as desired, by drop in filters.
15. Use of digital focus and zoom to allow better review of areas of interest and more detailed examination.
16. High rate of speed for the exam. Under ½ second.
17. Removal of measurement variables due to high speed and removal of averaging due to saccadic eye movement.
18. Optional removal of the use of a placido, now required in some systems.
19. Full interaction with the device and processor, better error communication and handling.
20. Internet options for better instrument performance measurement.

Those having ordinary skill in the relevant art will appreciate the advantages provide by the features of the present disclosure.

In the foregoing Detailed Description, various features of the present disclosure may be grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A system for aiding in an eye examination, said system comprising:
    a first light source;
    an optical semiconductor capable of selectively transmitting light from the first light source;
    one or more lenses for focusing the light transmitted from the optical semiconductor directly onto the eye;
    a source device for transmitting an image code to the optical semiconductor such that the optical semiconductor forms a predetermined image onto the eye through the one or more lenses;
    a first camera positioned to capture images of the predetermined image formed on the eye;
    a second camera positioned to capture images of the predetermined image formed on the eye;
    a pair of beam splitting cubes for directing a portion of light patterned on the eye to the second camera;
    a second light source for forming an image observable by the eye, light from said second light source traveling through said pair of beam spitting cubes to the eye; and
    a third light source for providing base line light levels.

2. The system of claim 1 wherein the optical semiconductor comprises a micromicron device.

3. The system of claim 1 wherein the optical semiconductor comprises a micromirror device on a chip.

4. The system of claims 2 or 3 wherein the micromicron device comprises an array of micromirrors mounted on tiny hinges.

5. The system of claims 2 or 3 wherein the micromirrors are controlled by the image code.

6. The system of claim 1 wherein the optical semiconductor transmits the light by reflection.

7. The system of claim 6 wherein the light is selectively reflected.

8. The system of claim 4 wherein the array is 1024×768.

9. The system of claim 1 further comprising electronic memory for storing the image code in a digital format.

10. The system of claim 1 wherein the optical semiconductor comprises an array of movable micromirrors.

11. The system of claim 10 wherein each micromirror is independently controllable.

12. The system of claim 10 wherein each micromirror's tilt angle is controllable.

13. The system of claim 10 wherein each micromirror is independently controlled by loading data into a memory cell located below the micromirror.

14. The system of claim 12 wherein the tilt angle for each micromirror may be selectively controlled between an OFF state and an ON state, the micromirror not reflecting light through the one or more lenses in the OFF state and reflecting light through the one or more lenses in the ON state.

15. The system of claim 10 wherein each micromirror is independently addressable.

16. The system of claim 1 further comprising a light dump.

17. The system of claim 1 further comprising a color wheel or a colored filter.

18. The system of claim 1 further comprising a prism.

19. The system of claim 1 wherein no mechanical aperture device is used.

20. The system of claim 1 wherein the system comprises an architecture selected from the group consisting of telecentric architecture and non-telecentric architecture.

21. The system of claim 1 further comprising one or more image capturing devices for capturing images of illuminated areas of the eye.

22. The system of claim 1 wherein the predetermined image is rectangular in shape.

23. The system of claim 1 further comprising structure for receiving a part of the human head.

24. A device for assisting in examining eyes of humans or animals, said device comprising:
   a first light source capable of emanating light;
   a micromicron device for selectively reflecting light emanating from the first light source in a predetermined image;
   a focusing system for focusing the predetermined image from the micromicron device directly onto an eye;
   a first camera positioned to capture images of the predetermined image on the eye;
   a second camera positioned to capture images of the predetermined image on the eye;
   a pair of beam splitting cubes for directing a portion of light patterned on the eye to the second camera;
   a second light source for forming an image observable by the eye, light from said second light source traveling through said pair of beam spitting cubes to the eye; and
   a third light source for providing base line light levels.

25. The device of claim 24 wherein the micromicron device comprises an array of micromirrors.

26. The device of claim 25 wherein each micromirror is independently addressable.

27. The device of claim 25 wherein the array is 1024×768.

28. The device of claim 25 wherein each mircomirror is mounted on a hinge.

29. The system of claim 25, 26, 27 or 28 wherein a tilt angle for each mircomirror may be selectively controlled between an OFF state and an ON state, the mircomirror not reflecting light through the focusing system in the OFF state and reflecting light through the focusing system in the ON state.

30. The system of claim 25 wherein each mircomirror may be controlled by software.

31. The system of claim 25 further comprising a microprocessor capable of controlling each micromirror.

32. The system of claim 24 further comprising a color wheel for projecting light of differing wavelengths onto the eye.

33. The system of claim 24 further comprising an electronic storage medium for storing the predetermined image in a digital format.

34. The system of claim 24 further comprising an electronic storage medium having a plurality of images stored thereon in a digital format, and wherein the predetermined image is selected from the plurality of images stored on the electronic storage medium.

35. The system of claim 24 further comprising a means for detecting degradation of the light source.

36. The system of claim 24 wherein the light source is chosen from the group consisting of an LED lamp or a halogen lamp.

37. The system of claim 24 further comprising an image capturing device for capturing images of illuminated areas of the eye.

38. The system of claim 37 further comprising a display device for displaying images captured by the image capturing device.

39. A system for assisting in examining eyes of humans or animals, said device comprising:
   a first light source capable of emanating light;
   an electronic storage medium having one or more images stored therein in a digital format;
   an electronic input device for allowing a person to select one of the images stored in the electronic storage medium;
   a micromicron device for reflecting the light emanating from the first light source in an image selected by the person via the electronic input device;
   and a focusing system for focusing the image reflected from the micromicron device onto an eye;
   a first camera positioned to capture images of the selected image on the eye;
   a second camera positioned to capture images of the selected image on the eye;
   a pair of beam splitting cubes for directing a portion of light patterned on the eye to the second camera;
   a second light source for forming an image observable by the eye, light from said second light source traveling through said pair of beam spitting cubes to the eye; and
   a third light source for providing base line light levels.

40. The system of claim 39 wherein the electronic input device is selected from the group consisting of a keyboard, a computer mouse, a touchscreen, and a voice recognition system.

41. The system of claim 39 further comprising an image capture device for capturing images of illuminated areas of the eye.

42. The system of claim 41 further comprising a display for displaying the images captured by the image capture device.

43. The system of claim 41 wherein the image capture device is a still camera or a video camera.

44. The system of claim 41 wherein the image capture device is a high speed camera.

45. The system of claim 39 wherein at least one of the images stored on the electronic storage medium is a rectangular image.

46. The system of claim 39 further comprising an electronic database for storing the images captured by the first and second cameras.

* * * * *